(12) United States Patent
Cueman et al.

(10) Patent No.: US 8,383,164 B2
(45) Date of Patent: Feb. 26, 2013

(54) ANTIVIRAL COMPOSITION AND METHOD FOR USING THE SAME

(75) Inventors: Glenn Fletcher Cueman, Denver, NC (US); Kenneth Robert Vest, Davidson, NC (US); Barnwell Samuel Ramsey, Huntersville, NC (US)

(73) Assignee: Innovasource LLC, Huntersville, NC (US)

( * ) Notice: Subject to any disclaimer, the term of this patent is extended or adjusted under 35 U.S.C. 154(b) by 469 days.

(21) Appl. No.: 12/493,796

(22) Filed: Jun. 29, 2009

(65) Prior Publication Data

US 2010/0330195 A1 Dec. 30, 2010

(51) Int. Cl.
*A61K 31/04* (2006.01)
*A61K 31/055* (2006.01)
*A61K 33/00* (2006.01)
*A61K 47/00* (2006.01)
*A01N 25/00* (2006.01)
*A01N 31/08* (2006.01)
*A01N 33/02* (2006.01)
*A01N 59/00* (2006.01)
*A61P 31/12* (2006.01)

(52) U.S. Cl. ........ 424/616; 514/649; 514/737; 514/788; 514/873

(58) Field of Classification Search .................. None
See application file for complete search history.

(56) References Cited

U.S. PATENT DOCUMENTS

| 5,661,170 A | 8/1997 | Chodosh |
| 5,827,870 A | 10/1998 | Chodosh |
| 6,503,952 B2 | 1/2003 | Modak et al. |

FOREIGN PATENT DOCUMENTS

| WO | WO 2008071746 A1 * | 6/2008 |
| WO | WO 2008135085 A1 * | 11/2008 |

* cited by examiner

*Primary Examiner* — James H. Alstrum-Acevedo
*Assistant Examiner* — Frank Choi
(74) *Attorney, Agent, or Firm* — Gregory N. Clements; Clements Bernard PLLC

(57) ABSTRACT

The present invention provides an antiviral composition and system for using the same, wherein the antiviral composition includes between about 0.1 to about 0.3 wt % of antimicrobial agent such as benzalkoniumchloride, between about 0.1 to about 1 wt % of chlorinated phenol compound, such as parachlorometaxylenol, between about 0.1 to about 3 wt % of hydrogen peroxide, and at least about 60 wt % aqueous solvent.

9 Claims, No Drawings

ANTIVIRAL COMPOSITION AND METHOD FOR USING THE SAME

FIELD OF THE INVENTION

The present invention relates generally to an antiviral composition and method for using the same, and more generally relates to an antiviral composition and method for using the same comprising one or more antibacterial agents, such as a quaternary ammonium compound and or a chlorinated phenol compound, hydrogen peroxide, and an aqueous solvent. In the right proportions, the composition is a very powerful antiviral composition that is affective against the norovirus (the cruise ship virus).

BACKGROUND OF THE INVENTION

It is important to thoroughly and effectively wash one's hands to prevent the spread of diseases and viruses. Illness caused by hands contaminated with pathogens is well recognized and documented in the food service industry. It is estimated that 30% of all food-borne illness is caused by pathogens being transferred from contaminated hands to food and subsequently being ingested by the host. Contaminated hands are the major source for spreading food-borne illness caused by viral infections (e.g. Hepatitis A, Norovirus Gastroenteritis, and Rotavirus Gastroenteritis), some bacterial infections (e.g. Shigellosis, Staphylococcal Gastroenteritis, and Hemorrhagic Colitis), as well as some parasitic infections (e.g. Giardia Duodenalis, Toxoplasmosis, Intestinal Cryptosporidiosis, and Cyclosporiasis). Alcohol based hand sanitizers are a quick, efficient, and popular way to reduce the microbial concentration on one's hands. These alcohol based hand sanitizers are so popular they are ubiquitous in hospitals, day care centers, and the like. The ease of use without the need for an adequate supply of flowing water has made the sanitizers very popular.

The problem with alcohol based sanitizers is they leave your skin dry and susceptible to cracking. Cracking skin provides places for bacteria to hide in, thus aggravating the problem. Another problem is that the alcohol sanitizers are very flammable and storing large quantities (like a hospital would have) requires a secure and fireproof room. Alcohol based sanitizers also serves as a source of alcohol for the alcohol dependent person. Alcohol based hand sanitizers can kill some viruses, but do not kill the dreaded norovirus. For all the above reasons, there is a need to create an alcohol-free sanitizer.

New formulations of alcohol-free based hand sanitizers have been developed that utilize benzalkonium chloride (BZK) in an aqueous solution that incorporates emollients that aid in protecting the skin after frequent use. These new formulations are beneficial because of their relative lack of toxicity and skin irritation, even after frequent long term use.

U.S. Pat. No. 5,827,870 and 5,661,170, to Chodosh, discloses an antimicrobial "SAB" composition that treats microbial infections. The antimicrobial composition includes a quaternary ammonium compound in an aqueous solution, wherein the preferred quaternary ammonium compound is benzalkonium chloride (BZK). The antimicrobial composition also contains a surfactant and the keratolytic agent allantoin (SAB=surfactant, allantoin, and BZK). The composition disclosed is solely antimicrobial in nature and is ideally suited for subcutaneous, cutaneous, or mucosal membrane administration.

U.S. Pat. No. 6,503,952 to Modak et al discloses a triple antimicrobial composition having chlorhexidine (or a salt thereof), a quaternary ammonium compound such as BZK, and a chlorinated phenol compound such as parachlorometaxylenol. Optionally alcohol may be included. This composition is stated to be antimicrobial, but it is silent with respect to reducing or controlling viruses.

The prior art has disadvantages. The prior art fails to reduce, control or eliminate certain viruses especially the norovirus (the cruise ship virus) and other similar viruses. There is a need for an antiviral hand sanitizer that is nontoxic and does not irritate the skin after frequent, long term use and is alcohol-free.

BRIEF SUMMARY OF THE INVENTION

The present invention provides an alcohol-free antiviral composition that includes between about 0.1 to about 3 wt % of hydrogen peroxide, between about 0.1 to about 0.3 wt % of an antibacterial agent, between about 0.1 to 1 wt % of a chlorinated phenol compound, and at least about 60 wt % aqueous solvent.

According to yet another embodiment of the present invention, the antiviral composition includes emollients.

According to yet another embodiment of the present invention, the antiviral composition includes benzalkonium chloride (also known as BZK) as the antibacterial agent.

According to yet another embodiment of the present invention, the antiviral composition includes parachlorometaxylenol (also known as PCMX) as the chlorinated phenol compound.

According to yet another embodiment of the present invention, the antiviral composition includes between about 0.1 to about 0.3 wt % of an antibacterial agent, between about 0.1 to about 3 wt % of hydrogen peroxide, and at least about 60 wt % aqueous solvent.

According to yet another embodiment of the present invention, the antiviral composition includes between about 0.1 to about 5 wt % of allantoin as an emollient.

Another embodiment of the present invention provides an alcohol-free antiviral composition that includes between about 0.1 to about 0.3 wt % of BZK, between about 0.1 to 1 wt % of PCMX, between about 0.1 to 3 wt. % hydrogen peroxide, and at least about 60 wt % aqueous solvent.

According to yet another embodiment of the present invention, a method of treating a virus includes applying an antiviral composition to an individual's hands or other potentially effected areas that includes between about 0.1 to about 0.3 wt % of a benzalkonium chloride, between about 0.1 and about 1 wt % of parachlorometaxylenol, between about 0.1 to 3 wt. % hydrogen peroxide, and at least about 60 wt % aqueous solvent, and repeating the administration of the antiviral composition to the hands when needed.

DETAILED DESCRIPTION OF THE INVENTION

The present invention provides an alcohol free antiviral composition that has a relative lack of toxicity and reduces skin irritation, even after frequent long term use. The composition may be used on cruise ships, hospitals, schools and like for preventing and reducing the spread of viral bodies. The present invention, depending on the composition, kills about 90% to about 99.9% of norovirus after a 15 second exposure to the composition.

The most preferred embodiment of the present invention, that kills 99.9% norovirus includes between about 0.1 to about 3 wt % of hydrogen peroxide, between about 0.1 to about 0.3 wt % of BZK, between about 0.1 to 1 wt % of a PCMX, and at least about 60 wt % aqueous solvent.

Other preferred compositions that kill between 90% and 99% of the norovirus and/or other common viruses include either: 1) between about 0.1 to about 3 wt % of hydrogen peroxide, between about 0.1 to about 0.3 wt % of BZK, and at least about 60 wt % aqueous solvent; or 2) between about 0.1 to about 3 wt % of hydrogen peroxide, between about 0.1 to 1 wt % of a PCMX, and at least about 60 wt % aqueous solvent.

The antibacterial agent in the present invention is preferably a quaternary ammonium compound, such as benzalkonium chloride (BZK), benzethonium chloride, methylbenzethonium chloride, and didecyldioctyl ammonium chloride. Other agents include miconazole, ketoconazole, clotrimazole, econazole, oxiconazole, isoconazole, triazoles, tolnaftate, naftifine hydrochloride, terbinafine hydrochloride, ciclopirox olamine, and haloprogin. Preferably, BZK is the antibacterial agent. The concentration of the quaternary ammonium compound present in the antiviral composition ranges from about 0.1 to about 5 wt % and all points therebetween. Depending on the antimicrobial agent or agents employed, and the other ingredients combined with them, the range is generally between 0.1 and 0.5 wt. %, and all points therebetween. With the most preferred embodiment, using BZK, the range is 0.1 to 0.3 wt. %, and all points therebetween. All wt. % are based on the total wt. of all ingredients in the antiviral composition.

A biguanide compound may be incorporated into the antiviral composition. The biguanide compounds exhibit germicide and antimicrobial properties that may be useful in applications of the antiviral composition. The biguanide compounds may include, but are not limited to, chlorhexidine free base, chlorhexidine diphosphanilate, chlorhexidine digluconate, chlorhexidine diacetate, chlorhexidine dihydrochloride, chlorhexidine dichloride, chlorhexidine dihydroiodide, chlorhexidine diperchlorate, chlorhexidine dinitrate, chlorhexidine sulfate, chlorhexidine sulfite, chlorhexidine thiosulfate, chlorhexidine di-acid phosphate, chlorhexidine difluorophosphate, chlorhexidine diformate, chlorhexidine dipropionate, chlorhexidine diiodobutyrate, chlorhexidine di-n-valerate, chlorhexidine dicaproate, chlorhexidine malonate, chlorhexidine succinate, chlorhexidine malate, chlorhexidine tartrate, chlorhexidine dimonoglycolate, chlorhexidine monodiglycolate, chlorhexidine dilactate, chlorhexidine di-$\alpha$-hydroxyisobutyrate, chlorhexidine diglucoheptonate, chlorhexidine di-isothionate, chlorhexidine dibenzoate, chlorhexidine dicinnamate, chlorhexidine dimandelate, chlorhexidine di-isophthalate, chlorhexidine di-2-hydroxynapthoate, chlorhexidine embonate, polyhexamethylene biguanide ("PHMB"), and alexidine (N,N"-Bis(2-ethylhexyl)-3,12-diimino-2,4,11,13-tetraazatetradecanediimidamine; 1,1'hexamethyl-enebis [5-(2-ethylhexyl)biguanide]). Preferably, the antiviral composition may contain between about 0.1 to 2 wt % of the biguanide compound, including all points therebetween.

Chlorinated phenol compounds may be added to the composition. The chlorinated phenols may include, but are not limited to, parachlorometaxylenol (PCMX), triclosan (2,4,4'-trichloro-2 hydroxy di-phenyl ether), 2-chlorophenol, 3-chlorophenol, 4-chlorophenol, 2,4-dichlorophenol, 2,4,6-trichlorophenol, 2,3,4,6-tetrachlorophenol, pentachlorophenol, 4-chlororesorcinol, 4,6-dichlororesorcinol, 2,4,6-trichlororesorcinol, alkylchlorophenols (including p-alkyl-o-chlorophenols, o-alkyl-p-chlorophenols, dialkyl-4-chlorophenol, and tri-alkyl-4-chlorophenol), dichloro-m-xylenol, chlorocresol, o-benzyl-p-chlorophenol, 3,4,6-trichlorphenol, 4-chloro-2-phenylphenol, 6-chloro-2-phenylphenol, o-benzyl-p-chlorophenol, and 2,4-dichloro-3,5-diethylphenol. Preferably, PCMX is utilized as the chlorinated phenol. The chlorinated phenol is present in the composition in the amount of between about 0.1 to 2 wt %, including all points therebetween. With the most preferred embodiment, using PCMX, the range is 0.1 to 1 wt. %, and all points therebetween, based on the total wt. of all the ingredients in the antiviral composition.

A skin protectant, such as allantoin, may be incorporated into the antiviral composition for protecting the skin. The allantoin increases the desirability of the antiviral composition. Antiviral compositions composed of BZK incorporate allantoin into the composition since other keratolytic agents are incompatable with most quaternary ammonium compounds. Keratolytic agents that may be used include, but are not limited to, triacetin, acetic acid, salicylic acid, polyoxyethylene lauryl ether, and panthenol. The skin protectant present in the antiviral composition is in the amount of from about 0.1% to about 5%, including all points therebetween.

A surfactant may be incorporated with the antimicrobial agent that is chemically compatible within the pH range of about 3 to about 9. In this pH range, the BZK is also stable. The surfactant is present in the composition in an amount of between about 0.1 to about 20 wt %, including all points therebetween. The surfactants that may be used in the present invention include alkanolamide, alkyl dimethylamine oxide, coconut monoethanolamide, cetyl dimethylamine oxide, stearamine oxide, olemine oxide, cocoamidopropyl dimethyl amine oxide, trimethyl cetyl quaternary ammonium chloride, trimethyl coco quaternary ammonium chloride, diquaternary polydimethylsiloxane, cetyl trimethyl ammonium chloride, cocoamido betaine, oleyl betaine, cocoamphodiacetate, cocamidopropyl hydroxysultaine, and cocoamidopropyl dimethyl betaine.

In another alternative embodiment, the antiviral composition may include a stabilizer or a thickening agent for increasing the viscosity of the composition. The viscosity of the composition can be adjusted depending upon the desires of the user. The stabilizers or thickening agents can be incorporated into the composition to adjust the viscosity of the composition. The range in which the stabilizer and thickening agent may be added will be known to one of skill in the art. Such stabilizers and thickening agents may include, but are not limited to, hydroxypropyl methylcellulose, hydroxypropyl cellulose, methyl cellulose, carboxy methylcellulose, emulsifying waxes, alkyl triammonium methosulfate, or ceteraryl octanoate.

The composition is preferably aqueous based, and utilizes distilled water as the solvent. At least about 60 wt % of distilled water is included in the composition. Alternatively, the composition may comprise at least 70 wt % of distilled water. Further alternatively, the composition may comprise at least 80 wt % of distilled water. In practice, once the amounts of the other ingredients are selected, the remainder is the distilled water. Thus the distilled water may comprise over 90 wt. % of the antiviral composition.

For the commercial industry, it is sometimes preferred that the antiviral composition include a preservative for preserving the shelf life of the antiviral composition. A person of ordinary skill in the art will understand the most effective and appropriate preservative to use for the desired application of the antiviral compound. The preservative does not function to inhibit the antimicrobial growth, as the ingredients already function in that manner. But the preservative functions to prevent undesirable chemical changes. Such preservative may include, but are not limited to, parabens, methyl paraben, propyl paraben, imidazolidinyl urea, diazolidinyl urea, and the cis isomer of 1-(3-chloroallyl)-3,5,7-triaza-1-azoniaadamantane chloride. Preferably, the amount of preservative in the antiviral composition is between about 0.1 wt % and 1.5 wt %, including all points therebetween.

In yet another preferred embodiment, the antiviral composition may include a scrub base. The scrub base can aid in the application of the present invention to kill viruses and intended microbes. The base may comprise between about 10 to about 30 wt % of a pluronic copolymer surfactant, about 1 to about 5 wt % of an amine oxide foaming agent, about 0.1 to about 1 wt % chlorinated phenol, about 0.1 to about 0.3 wt % of an antibacterial agent, and an aqueous solvent. A mild acid may be used to adjust the pH of the scrub. Such acids that have been found to be effective include, but are not limited to, gluconolactone, lactic acid, salicylic acid, citric acid, or gluconic acid. An organic solvent may also be introduced to aid in the dissolution of the antibacterial agent. Preferably, the antibacterial agent is BZK and the chlorinated phenol is PCMX.

In yet another preferred embodiment, the antiviral composition may include a scrub base contained hydrogen peroxide. The scrub base can aid in the application of the present invention to kill viruses and intended microbes. The base may comprise between about 10 to about 30 wt % of a pluronic copolymer surfactant, about 1 to about 5 wt % of an amine oxide foaming agent, about 0.1 to about 3 wt % hydrogen peroxide, about 0.1 to about 0.3 wt % of an antibacterial agent, and an aqueous solvent. A mild acid may be used to adjust the pH of the scrub. Such acids that have been found to be effective include, but are not limited to, gluconolactone, lactic acid, salicylic acid, citric acid, or gluconic acid. An organic solvent may also be introduced to aid in the dissolution of the antibacterial agent. Preferably, the antibacterial agent is BZK and between about 0.1 to about 1 wt % of a chlorinated phenol may be introduced to the scrub. Preferably, the chlorinated phenol is PCMX

EXAMPLES

The antiviral composition is generally prepared by blending the constituents together into a homogenous mixture. The following examples exemplify the antiviral composition as made.

Example 1

In one embodiment of the present invention, the composition was formed by blending 0.13 wt % of BZK, 0.5 wt % PCMX, 3 wt % hydrogen peroxide, and distilled water, forming a homogenous mixture.

Example 2

In yet another embodiment of the present invention, the composition was formed by blending 0.13 wt % of BZK, 1 wt % PCMX, 3 wt % hydrogen peroxide, and distilled water, forming a homogenous mixture.

Example 3

In another embodiment of the present invention, the composition is formed by blending 0.13 wt % of BZK, 3 wt % of hydrogen peroxide, and distilled water, forming a homogenous mixture.

Example 4

In yet another embodiment of the present invention, the composition was formed by blending 1 wt % PCMX, 3 wt % hydrogen peroxide, and distilled water, forming a homogenous mixture.

Specimens of the norovirus (murine Norovirus) were exposed (via the Viral Suspension Test) to each of the antiviral composition exemplified in the Examples above. The norovirus was exposed to the antiviral composition for 15 seconds, after which time the norovirus was examined to determine the effects of the antiviral composition on the norovirus. Upon examination, the solution in Examples 3 and 4 significantly improved the reduction of the norovirus by killing about 90% of the norovirus after the 15 second exposure. The antiviral composition in Examples 1 and 2 killed 99.9% of the norovirus after the 15 second exposure, (resulting in a 3+ log reduction) because there is a true synergy with the combination of hydrogen peroxide, BZK, and PCMX. The composition of Example 3 was also exposed to feline Caliciovirus for 15 seconds and resulted in a 1 log reduction of the virus compared to "no effect" when using just 0.13 wt % BZK in distilled water.

The antiviral composition may be incorporated into a variety of products, including hand sanitizers. Other products include, but are not limited to, soaps, sprays, lotions, topical creams, topical disinfectants, antiseptic rinses, antiseptic soaks, antiseptic wipes, and antiseptic towellettes.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention and are intended to be covered by the following claims.

What is claimed is:

1. An antiviral composition comprising: antimicrobial agents, aqueous solvent, and optionally at least one ingredient that has no effect on microbes, including viruses, said antimicrobial agents, based on the total weight of said composition, consisting essentially of:
    a) between about 0.1 to about 0.3 wt % of benzalkoniumchloride;
    b) between about 0.1 to about 1 wt % of parachlorometaxylenol; and
    c) between about 0.1 and about 3 wt % of hydrogen peroxide;
and said aqueous solvent being present in said composition at least about 60 wt %.

2. An antiviral composition comprising: antimicrobial agents, aqueous solvent, and optionally at least one ingredient that has no effect on microbes, including viruses, said antimicrobial agents, based on the total weight of said composition, consisting essentially of:
    a) between about 0.1 to about 0.15 wt % of benzalkoniumchloride;
    b) between about 0.75 to about 1 wt % of parachlorometaxylenol; and
    c) between about 2 and about 3 wt % of hydrogen peroxide;
and said aqueous solvent being present in said composition at least about 60 wt %.

3. The antiviral composition according to claim 1, said optional ingredient comprising skin emollients.

4. The antiviral composition according to claim 3, wherein said skin emollient comprises between about 0.1 to about 5 wt % of allantoin.

5. The antiviral composition according to claim 1, said optional ingredient comprising between about 0.1 to about 20 wt % of a surfactant.

6. A method of treating a virus, comprising:
    applying an antiviral composition to an individual's hands, comprising antimicrobial agents, aqueous solvent, and optionally at least one ingredient that has no effect on microbes, including viruses, said antimicrobial agents, based on the total weight of said composition, consisting essentially of:
(1) between about 0.1 to about 0.15 wt % of benzalkoniumchloride;
(2) between about 0.75 and about 1 wt % of parachlorometaxylenol; and
(3) between about 2 to about 3 wt % of hydrogen peroxide; and said aqueous solvent being present in said composition at least about 60 wt %; and re-applying said antiviral composition to the hands when needed.

7. The method according to claim 6, wherein the antiviral composition further comprises a skin emollient.

8. The method according to claim 7, wherein said skin emollient comprises from about 0.1 to about 5 wt % allantoin.

9. The method according to claim 6, wherein the antiviral composition further comprises between about 0.1 and about 20 wt % of surfactant.

* * * * *